(12) United States Patent
Ryan et al.

(10) Patent No.: US 11,083,465 B2
(45) Date of Patent: Aug. 10, 2021

(54) AGGRESSIVE FEATURED CLIPS WITH IMPROVED TISSUE RETENTION

(71) Applicant: BOSTON SCIENTIFIC SCIMED, INC., Maple Grove, MN (US)

(72) Inventors: Shawn Ryan, Littleton, MA (US); Irina Pyataeva, Roxbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 141 days.

(21) Appl. No.: 16/564,822

(22) Filed: Sep. 9, 2019

(65) Prior Publication Data
US 2020/0093496 A1 Mar. 26, 2020

Related U.S. Application Data

(60) Provisional application No. 62/735,728, filed on Sep. 24, 2018.

(51) Int. Cl.
*A61B 17/122* (2006.01)
*A61B 17/128* (2006.01)
(Continued)

(52) U.S. Cl.
CPC ...... *A61B 17/1227* (2013.01); *A61B 17/1285* (2013.01); *A61B 2017/0034* (2013.01); *A61B 2017/12004* (2013.01)

(58) Field of Classification Search
CPC ....... A61B 17/08; A61B 17/083; A61B 17/10; A61B 17/122; A61B 17/1227; A61B 17/128; A61B 17/1285; A61B 2017/12004
See application file for complete search history.

(56) References Cited

U.S. PATENT DOCUMENTS 5,015,249 A * 5/1991 Nakao ..................... A61B 17/10
227/901
5,049,153 A * 9/1991 Nakao ..................... A61B 17/10
606/151
(Continued)

FOREIGN PATENT DOCUMENTS

EP  2 455 099  5/2012

OTHER PUBLICATIONS

Akimoto et al., "Endoscopic closure after intraluminal surgery," Digestive Endoscopy, Japan Gastroenterological Endoscopy Society, No. 29, 2017, pp. 547-558.
(Continued)

*Primary Examiner* — Ryan J. Severson
(74) *Attorney, Agent, or Firm* — Fay Kaplun & Marcin, LLP

(57) ABSTRACT

A system for treating tissue includes a capsule including a channel extending therethrough; first and second clip arms each extending from a proximal end to a distal end, the proximal ends being received within the channel of a capsule to be moved between an open tissue receiving configuration; and a closed tissue clipping configuration. The first clip arm includes a first tissue retention feature at a distal portion thereof configured to pierce through a target tissue when in the tissue clipping configuration and subsequently release the target tissue when the clip arms are moved to an at least partially open configuration. The second clip arm includes a second tissue retention feature at a distal portion thereof configured to pierce and retain the target tissue thereon when in both the closed tissue clipping configuration and the open tissue receiving configuration.

20 Claims, 5 Drawing Sheets

(51) Int. Cl.
*A61B 17/00* (2006.01)
*A61B 17/12* (2006.01)

(56) References Cited

U.S. PATENT DOCUMENTS

| | | | | |
|---|---|---|---|---|
| 6,991,634 | B2* | 1/2006 | Sugiyama | A61B 17/122 |
| | | | | 606/142 |
| 8,080,021 | B2* | 12/2011 | Griego | A61B 17/068 |
| | | | | 606/143 |
| 10,010,336 | B2* | 7/2018 | Martinez | A61B 17/29 |
| 10,588,635 | B2* | 3/2020 | Smith | A61B 17/00234 |
| 10,820,904 | B2* | 11/2020 | Ryan | A61B 17/1285 |
| 10,842,351 | B2* | 11/2020 | Osaka | A61B 1/00087 |
| 2002/0151916 | A1* | 10/2002 | Muramatsu | A61B 17/1285 |
| | | | | 606/158 |
| 2008/0140089 | A1* | 6/2008 | Kogiso | A61B 17/1285 |
| | | | | 606/142 |
| 2014/0379018 | A1* | 12/2014 | Martinez | A61B 17/08 |
| | | | | 606/185 |
| 2015/0018848 | A1* | 1/2015 | Kappel | A61B 17/083 |
| | | | | 606/140 |
| 2016/0242778 | A1* | 8/2016 | Xu | A61B 17/08 |
| 2017/0333040 | A1 | 11/2017 | Smith et al. | |
| 2018/0085122 | A1 | 3/2018 | Ryan et al. | |
| 2020/0093496 | A1* | 3/2020 | Ryan | A61B 17/10 |

OTHER PUBLICATIONS

Akimoto et al., ""Hold-and-drag" closure technique using repositionable clips for large mucosal effects after colonic endoscopic submucosal dissection," Endoscopy International Open 2016, No. 4, pp. E1068-E1072.

Fujii et al., "A novel endoscopic suturing technique using a specially designed so-called "8-ring" in combination with resolution clips", Castrointestinal Endoscopy, vol. 66, No. 6, 2007, pp. 1215-1220.

* cited by examiner

AGGRESSIVE FEATURED CLIPS WITH IMPROVED TISSUE RETENTION

PRIORITY CLAIM

The disclosure claims priority to U.S. Provisional Patent Application Ser. No. 62/735,728 filed Sep. 24, 2018; the disclosure of which is incorporated herewith by reference.

FIELD

The present disclosure relates to compression clips, and more specifically, to compression clips delivered to a target site through an endoscope to cause hemostasis of blood vessels along the gastrointestinal tract.

BACKGROUND

Pathologies of the gastrointestinal (GI) system, the biliary tree, the vascular system, and other body lumens and hollow organs are often treated through endoscopic procedures, many of which require hemostasis to control bleeding. Hemostasis clips grasp tissue surrounding a wound and hold edges of the wound together temporarily to allow natural healing processes to permanently close the wound. Specialized endoscopic clipping devices are used to deliver the clips at desired locations within the body after which the clip delivery device is withdrawn, leaving the clip within the body. In addition to providing hemostasis, endoscopic clipping devices may also be used to provide, for example, endoscopic marking and closure of luminal perforations, e.g., from endoscopic procedures involving access to internal tissue by passing a device through a wall of a natural body lumen.

The opening width of the clips usually determine a maximum size of a defect that it can potentially close. To close a defect larger than a maximum clip opening width, several sophisticated closure techniques have been developed that often require the additional use of snares, "8 rings", or other devices. As an alternative to these advanced and technically challenging methods, a novel technique for defect closure uses a technique known colloquially "hold and drag" that makes it possible to close sizable defects using only conventional clips. This technique simplifies the closure of large defects and reduces the time required for the procedure. However, the biggest challenge in using this technique is the high risk of tissue slipping out if a clip is reopened. As a result, it is not uncommon that many attempts are required for the successful closure of defects when applying this technique.

SUMMARY

The present disclosure relates to a system for treating tissue comprising a capsule extending longitudinally from a proximal end to a distal end and including a channel extending therethrough and first and second clip arms each extending from a proximal end to a distal end, the proximal ends being received within a channel of a capsule to be moved between an open tissue receiving configuration, in which distal ends of the clip arms are separated from one another, and a closed tissue clipping configuration, in which distal ends of the clip arms are moved toward one another, wherein the first clip arm includes a first tissue retention feature at a distal portion thereof configured to pierce through a target tissue when in the tissue clipping configuration and subsequently release the target tissue when the clip arms are moved to an at least partially open configuration and the second clip arm includes a second tissue retention feature at a distal portion thereof configured to pierce and retain the target tissue thereon when in both the closed tissue clipping configuration and the open tissue receiving configuration.

In an embodiment, the first tissue retention feature includes a single spike at a distal tip of the first arm and the second tissue retention feature includes two spikes at a distal tip of the second arm.

In an embodiment, the spikes extend from the distal tips of the first and second arms at a 90 degrees angle relative to the longitudinal axis of the clip arms.

In an embodiment, when the clip arms are in the closed configuration, spikes on opposing clip arms are configured to be staggered.

In an embodiment, the first tissue retention feature includes at least one spike at a distal tip of the first arm and the second retention feature is a hook extending from the distal tip of the second arm.

In an embodiment, the second tissue retention feature includes a plurality of barbs extending from an interior surface of the second clip arm.

In an embodiment, the barbs extend at a 90 degrees angle relative to a longitudinal axis of the second clip arm.

The present disclosure also relates to a reloadable clip device comprising an applicator including a catheter and a control member extending therethrough, the control member extending from a proximal end to a distal end and being longitudinally movable relative to the applicator, at least one clip assembly coupled to the applicator, each clip assembly comprising: a capsule extending longitudinally from a proximal end to a distal end and including a channel extending therethrough, and first and second clip arms each extending from a proximal end to a distal end, the proximal ends being received within a channel of a capsule to be moved between an open tissue receiving configuration, in which distal ends of the clip arms are separated from one another, and a closed tissue clipping configuration, in which distal ends of the clip arms are moved toward one another, wherein the first clip arm includes a first tissue retention feature at a distal portion thereof configured to pierce through a target tissue when in the tissue clipping configuration and subsequently release the target tissue when the clip arms are moved to an at least partially open configuration and the second clip arm includes a second tissue retention feature at a distal portion thereof configured to pierce and retain the target tissue thereon when in both the closed tissue clipping configuration and the open tissue receiving configuration.

In an embodiment, the first tissue retention feature includes a single spike at a distal tip of the first arm and the second tissue retention feature includes two spikes at a distal tip of the second arm.

In an embodiment, the spikes extend from the distal tips of the first and second arms at a 90 degrees angle relative to the longitudinal axis of the clip arms.

In an embodiment, when the clip arms are in the closed configuration, spikes on opposing clip arms are configured to be staggered.

In an embodiment, the first tissue retention feature includes at least one spike at a distal tip of the first arm and the second retention feature is a hook extending from the distal tip of the second arm.

In an embodiment, the second tissue retention feature includes a plurality of barbs extending from an interior surface of the second clip arm.

In an embodiment, the plurality of barbs extend at a 90 degrees angle relative to a longitudinal axis of the second clip arm.

In an embodiment, an interior surface of the first clip arm is flat.

The present disclosure also relates to a method of treating tissue comprising inserting a first clip assembly to a target site within a living body via a working channel of an endoscope, the first clip assembly including a capsule and first and second clip arms slidably received within the capsule to be movable between an open configuration, in which distal ends of the clip arms are separated from one another, and a closed configuration, in which distal ends of the clip arms are drawn toward on another, positioning the clip arms in contact with a first target tissue, moving the first clip assembly from the open configuration to the closed configuration such that a first tissue retention feature on a distal portion of the first clip arm and a second tissue retention feature on a distal portion of the second clip arm pierces through the first target tissue, moving the first clip assembly from the closed configuration to the open configuration, the first tissue retention feature releasing the first target tissue while the second tissue retention feature retains the first target tissue thereon, positioning the clip arms in contact with a second target tissue and moving the first clip assembly from the open configuration to the closed configuration to clip the first and second target tissues between the first and second clip arms.

In an embodiment, the first tissue retention feature is a spike.

In an embodiment, the second tissue retention feature is one of a plurality of barbs, a plurality of spikes and a hook.

In an embodiment, the method further comprises loading a first clip assembly on an applicator by coupling a control member of the applicator to the proximal ends of clip arms.

In an embodiment, the method further comprises releasing the clip assembly from the applicator and loading a second clip assembly on an applicator by coupling a control member of the applicator to the proximal ends of clip arms.

BRIEF DESCRIPTION

DETAILED DESCRIPTION

Figure 1:
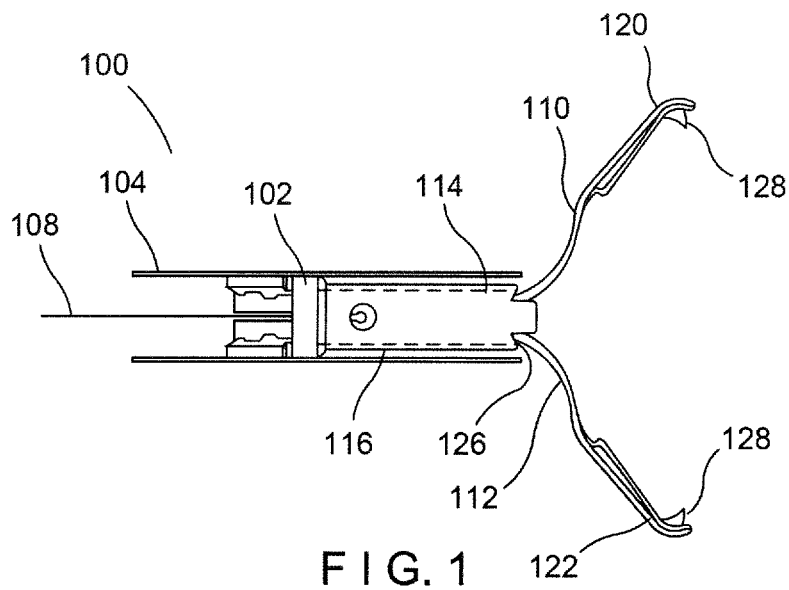
FIG. 1 shows a top plan view of a clip system according to an exemplary embodiment of the present disclosure.

The present disclosure may be further understood with reference to the following description and the appended drawings, wherein like elements are referred to with the same reference numerals. The present disclosure relates to a clipping system and, in particular, relates to a single use or reloadable endoscopic clipping system for treating tissue perforations, defects and/or bleeds. Exemplary embodiments of the present disclosure describe a hemostatic clip having aggressive gripping or retention features to improve attachment to target tissue when the clip is at least partially in an open configuration. In particular, exemplary embodiments describe a hemostatic clip with clip arms having spikes, hooks, barbs and other geometries as gripping features to allow grabbing and holding of tissue by a single clip arm. It should be noted that the terms "proximal" and "distal," as used herein, are intended to refer to toward (proximal) and away from (distal) a user of the device.

As shown in FIGS. 1, a system 100 according to an exemplary embodiment of the present disclosure comprises a clip assembly 102 insertable into a living body through, for example, a working channel of an endoscope to target tissue to be treated. The clip assembly 102 is sufficiently flexible to permit it to traverse a tortuous path through the body—e.g., passing through the working channel of a flexible endoscope inserted through a natural body lumen accessed via a natural bodily orifice. In an exemplary embodiment, the clip assembly 102 is loadable onto a distal portion of an applicator 104 prior to insertion of the clip assembly 102 into a living body for the clipping of target tissue. The applicator 104 and the clip assembly 102 are configured so that, after deployment of the clip assembly 102 in the living body, a new clip assembly 102 may be loaded onto the applicator 104 so that the same applicator 104 may be used to deliver a new clip assembly 102 to a second portion of target tissue in the living body. The applicator 104 may include a catheter (not shown) and a control member 108 extending therethrough. The clip assembly 102 includes first and second clip arms 110, 112 slidably received within a longitudinal channel 114 of a capsule 116. The first and second clip arms 110, 112 can be moved between an open tissue receiving configuration, in which the distal ends 120, 122 of the clip arms 110, 112, respectively, are separated from one another to receive target tissue therebetween, and a closed tissue gripping configuration, in which the distal ends 120, 122 of the clip arms 110, 112 are moved toward one another to grip the target tissue therebetween. The clip arms 110, 112 are movable between the open and the closed configurations via the control member 108 extending into the capsule 116. A proximal end (not shown) of the control member 108 is connected to an actuator on a handle positioned outside of the human body. In this embodiment, a distal end of the control member 108 is coupled to proximal ends of the clip arms 110, 112.

As further shown in FIG. 1, the clip arms 110, 112 according to an exemplary embodiment of the present disclosure which extend from proximal ends (not shown) to the distal ends 120, 122. As those skilled in the art will understand, arms 110, 112 of this embodiment are biased toward an open tissue receiving position in which the distal ends 120, 122 are separated from one another to receive tissue. That is, the arms 110, 112 are formed so that they spring open to the tissue receiving position when they are moved distally out of the constraint of the capsule 116. However, as would be understood by those skilled in the art, the clip assembly 102 may include a separate member urging the clip arms 110, 112 away from one another in addition, or as an alternative, to this bias. In an exemplary embodiment, the clip arms 110, 112 may include locking tabs (not shown) at their proximal ends for engaging distal components within the capsule 116 when the clip assembly 102 has been deployed. Locking tabs (not shown) may also form a mechanical lock with windows formed on lateral sides of the capsule 116 after the clip has been deployed. However, those skilled in the art will understand that any of the various known mechanisms for releasably coupling a clip assembly 102 (e.g., a capsule including clip arms) to an insertion device may be employed without deviating from the scope of the invention. As indicated above, the clip arms 110, 112 are biased toward the open configuration so that, when the clip arms 110, 112 are moved distally past a distal end 126 of the capsule 116, distal ends 120, 122 of the clip arms 110, 112 separate from one another to the open configuration. When the clip arms 110, 112 are drawn proximally into the capsule 116, contact with the capsule 116 draws the clip arms 110, 112 toward one another to the closed configuration. Upon deployment, the clip arms 110, 112 are locked within the capsule 116 which holds them in the closed position as would be understood by those skilled in the art. As described above, the clip arms 110, 112 are moved between the open and closed configurations via the control member 108, which is moved proximally and distally relative to the capsule 116 via an actuator at a handle that remains outside the body.

Figure 2:
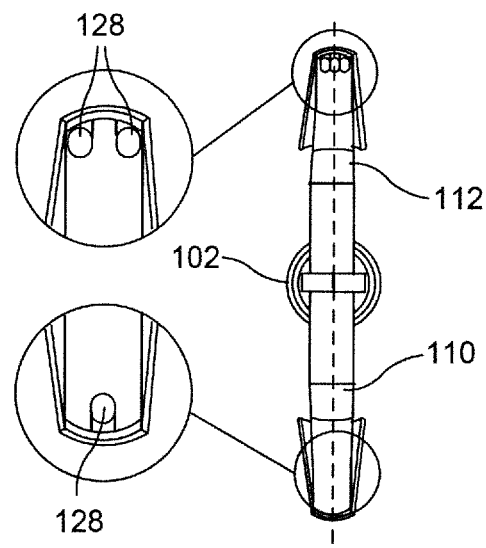
FIG. 2 shows a front view of a clip assembly of the clip system of FIG. 1.
Figure 3:
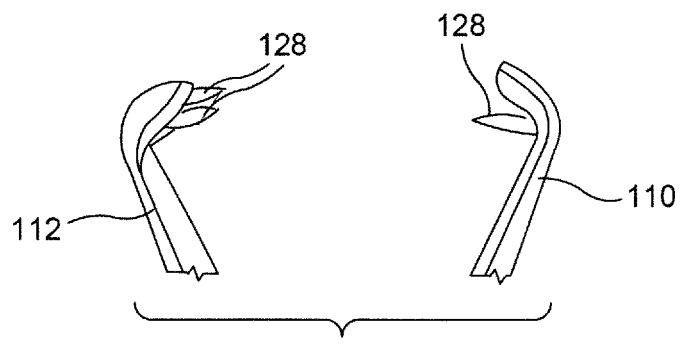
FIG. 3 shows a perspective view of distal ends of clip arms of the clip assembly of the clip system of FIG. 1.
Figure 4:
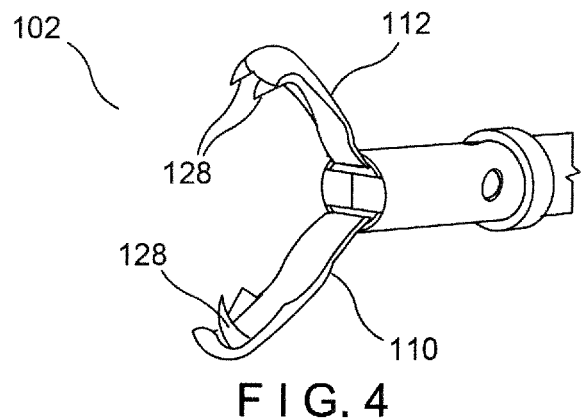
FIG. 4 shows a perspective view of the clip assembly of the clip system of FIG. 1.

In an exemplary embodiment, one or both of the clip arms 110, 112 may include spikes 128 extending from an interior side of a distal tip 130 of the clip arms 110, 112. As shown in FIGS. 2-3, the first clip arm 110 has a single spike 128 while the second clip arm 112 has two spikes 128. The spikes 128 extend substantially perpendicularly from the interior face of the clip arms 110, 112 radially inward toward the other of the clip arms 110, 112. In an exemplary embodiment, the spikes 128 are designed to pierce or at least engage the tissue such that the tension in the tissue (from pulling it across the defect) creates more engagement between the spikes 128 and the tissue. For example, a fishhook shape demonstrates this engagement once it pierces the tissue: application of additional force in the same direction pushes the tissue further up the hook while the direction of force must be reversed to remove the hook. As can be seen in FIG. 3, the spikes 128 on opposing anus 110, 112 are offset from one another longitudinally so that they do not prevent complete closure of the clip arms 110, 112 around the tissue defect. For example, as shown in FIG. 3, the spike 128 of the first clip arm 110 is positioned one of distally or proximally of the two spikes 128 on the second clip arm 112 when the clip assembly 102 is in the closed configuration. Furthermore, as shown in FIG. 4, the spikes of the first and second clip arms 110, 112 are offset from one another laterally so that the spike 128 of the first clip arm 110 is received between the spikes 128 of the second clip arm 112 without any interference. In an alternate embodiment, the spikes 128 are configured to extend in different planes to be received by an opposing arm without interference from the spike 128 of the other arm. For example, the spike 128 of the first clip arm 110 is positioned so that it fits between the two spikes 128 of the second clip arm 112 when the clip assembly 102 is in the closed configuration. In another embodiment, both of the spikes 128 are configured to extend in substantially the same plane so that when arms 110, 112 are in a closed configuration ends of the spikes 128 from opposing arms 110, 112 touch one another. As would be understood by those skilled in the art, the spikes 128 are sufficiently sharp to pierce through tissue and hook therein. In an embodiment, the spikes 128 of the second clip arm 112 are angled to a greater degree with respect to the rest of the clip arm 112 so that the spikes 128 remain hooked within the target tissue when the clip assembly 102 is moved to the open configuration to capture another portion of tissue. Specifically, the spikes 128 may likewise extend from the interior face of clip arm 112 at various angles between 20 and 90 degrees relative to the longitudinal axis L of the clip arm 112 to allow the spikes 128 to continue to grab the tissue when the clip arms 110, 112 are in the open configuration.

In use, the operator will orient the clip arms 110, 112 so that the second clip arm 112 will be on the outside of the tissue defect and the first clip arm 110 is on the inside of the tissue defect. Next, the operator will close the clip assembly 102 on the edge of the tissue defect and the spikes 128 will pierce through the mucosal layer to keep the tissue inside the clip anus 110, 112. When the clip assembly 102 is dragged to the opposite edge of the tissue defect and gently reopened, the tissue flap will still be hooked onto the second clip arm 112 but released from the first arm 110. That is, the direction of force of the first clip arm 110 is reversed so that the tissue is unclipped from the first clip arm 110 while remaining on the second clip arm 112. The first clip arm 110 can then be used to draw the opposite edge of the defect inside the clip assembly 102. The spikes 128 on both jaws 110, 112 will ensure that the edges of the defect are securely captured and will not slip out when the clip is closed and deployed. When the two opposing edges of the tissue defect are connected by the clip assembly 102, the clip assembly 102 will be released from the applicator 104 and further clips can be placed along the tissue defect to finalize the closure, as will be described in further detail below.

Figure 5:
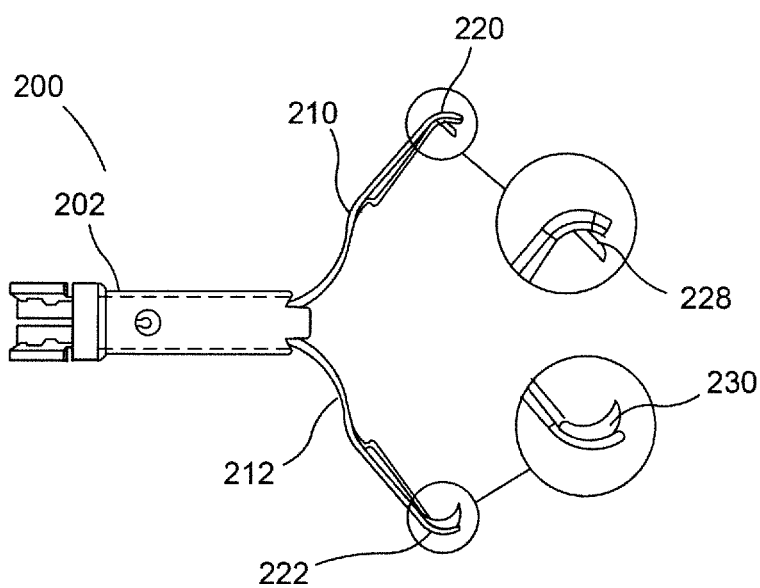
FIG. 5 shows a top plan view of a clip system according to a second exemplary embodiment of the present disclosure.
Figure 6:
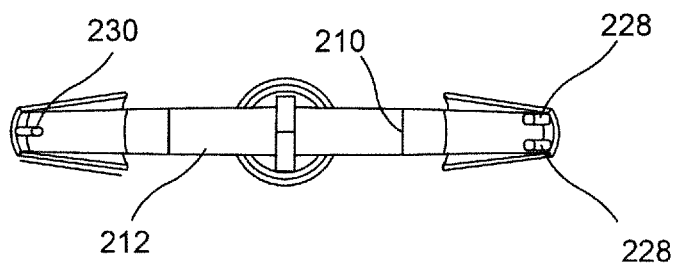
FIG. 6 shows a front view of a clip assembly of the clip system of FIG. 5.

In another exemplary embodiment, shown in FIGS. 5-6, a system 200 is substantially the same as system 100 except as described herein. The system 200 includes a clip assembly 202 with first and second clip arms 210, 212. In this embodiment, the clip arms 210, 212 use a combination of hooks and spikes to retain a first tissue edge on one arm while dragging a second tissue edge toward the first edge with the second arm. Specifically, as shown in FIG. 5, the first arm 210 includes two spikes 228, similar to the spikes 128 of the clip assembly 102, extending substantially perpendicularly from the interior face of the clip arm 210 radially inward toward the second clip arm 212. The second arm 212 has a hooked distal end 222 with a sharp distal-most tip 230 configured to pierce and retain tissue thereon. In an exemplary embodiment, the distal tip 230 is angled at approximately 90 to 180 degrees relative to the rest of the clip arm 212. For example, in an embodiment, the distal end 222 of the second clip arm 212 may be bent back toward the clip assembly 202 such the distal tip 230 is approximately parallel to the rest of the clip arm 212. This embodiment provides a high degree of tissue retention once the distal tip 230 has pierced the tissue defect. In another example, the distal end 222 may have a greater than 90 degree bend such that distal tip is substantially perpendicular to the proximal portion of the clip arm 212. This embodiment allows the tissue defect to be more easily pierced by the distal tip 230.

In use, the hooked distal end 222 of the second clip arm 212, as discussed above, is designed to adhere to the tissue and keep a first edge of the tissue defect inside the clip arms 210, 212 while the spike 228 of the first clip arm 210 is designed to release the first edge of the tissue defect and draw the opposite second edge of the tissue defect in when the clip assembly 202 is reopened. This combination of aggressive features has demonstrated to be especially effective for the "hold and drag" technique.

Figure 7:
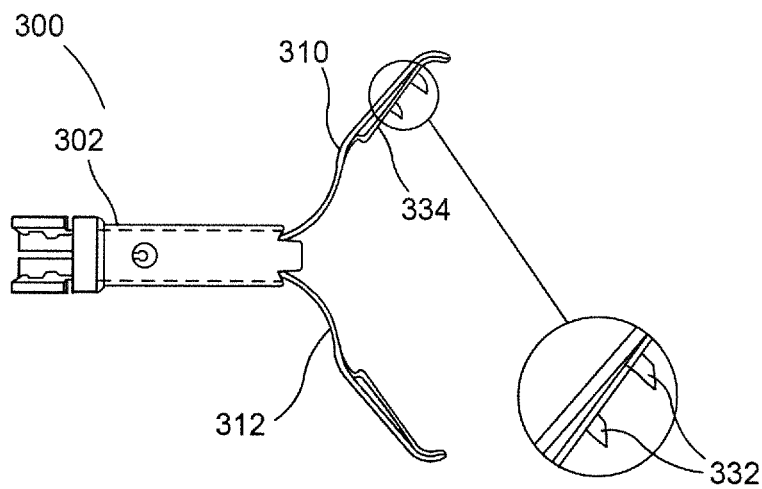
FIG. 7 shows a top plan view of a clip system according to a third exemplary embodiment of the present disclosure.
Figure 8:
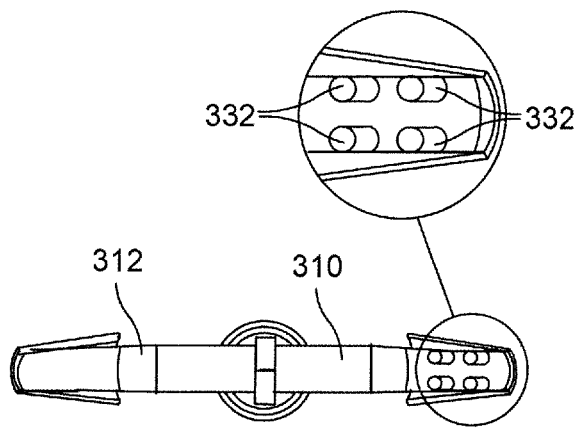
FIG. 8 shows a front view of a clip assembly of the clip system of FIG. 7.
Figure 9:
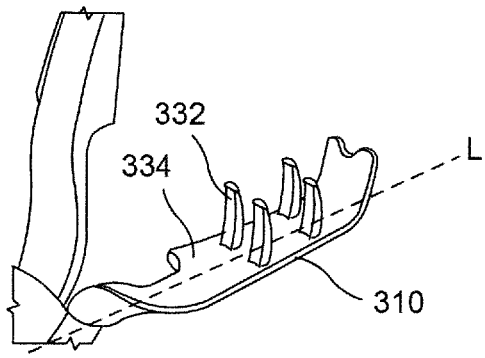
FIG. 9 shows a perspective view of distal ends of clip arms of the clip assembly of the clip system of FIG. 7.

In another exemplary embodiment, shown in FIGS. 7-9, a system 300 is substantially the same as systems 100, 200 except as described herein. The system 300 includes a clip assembly 302 with first and second clip arns 310, 312. The first clip arm 310, in this embodiment, includes one or more barbs 332 attached to an interior face 334 of a distal portion of the first clip arm 310. Clip arms with barbs are especially effective if the operator can force the barbed arm flat against the target tissue. This positioning of the arm flat against the tissue allows each of the barbs 332 to pierce the submucosal tissue layer and force the tissue to stay attached to the clip arm even under high tension. As shown in FIGS. 8-9, the first clip arm 310 of this embodiment includes four barbs 332 which extend substantially perpendicularly from the interior face 334 of the first clip arm 310 radially inward toward the second clip arm 312. It will be understood that while the present embodiment includes four barbs 332, any number of barbs may be used. The barbs 334 may likewise extend from the interior face 334 at various angles between 20 and 90 degrees and, more particularly, 45 degrees relative to the longitudinal axis L of the clip arm 310 to allow the barbs 332 to grab tissue when the clip arms 310, 312 are in the open configuration. That is, the barbs 332 may extend outward from the interior face 334 of the first clip arm 310 in a plane substantially perpendicular to a plane containing the interior face 334 of the first clip arm 310 or may extend at an angle and thus in a plane that is not perpendicular to the plane containing the interior face 334 of the clip arm 310. In an embodiment, shown in FIGS. 8-9 the barbs 332 are positioned on the interior face 334 as pairs that are substantially parallel with one another. However, it is understood that the barbs 332 may take any configuration such as, for example, longitudinally staggered pairs, a single longitudinal line along a central longitudinal axis of the clip arm 310, etc. As can be seen in the figures, the second arm 312 has a flat profile along its length.

Figure 10:
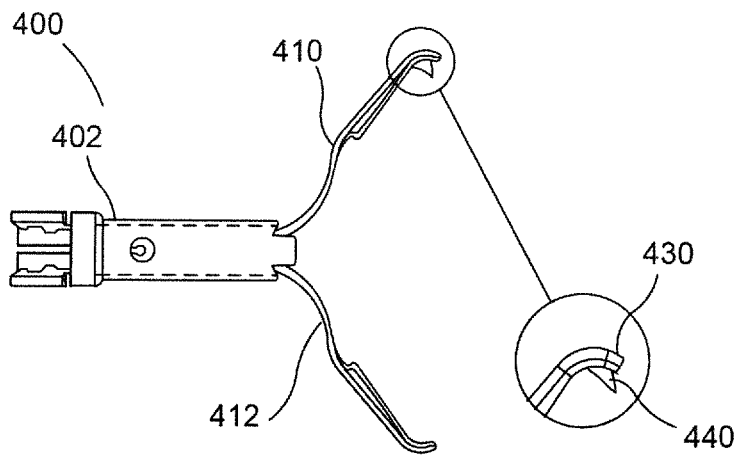
FIG. 10 shows a top plan view of a clip system according to a fourth exemplary embodiment of the present disclosure.
Figure 11:
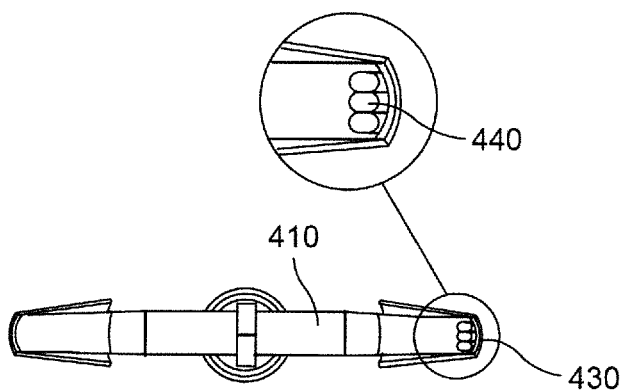
FIG. 11 shows a front view of a clip assembly of the clip system of FIG. 10.
Figure 12:
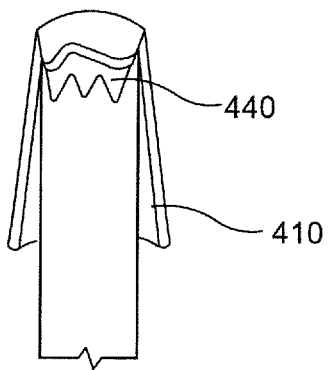
FIG. 12 shows a side view of the distal end of a clip arm of the clip assembly of the clip system of FIG. 10.
Figure 13:
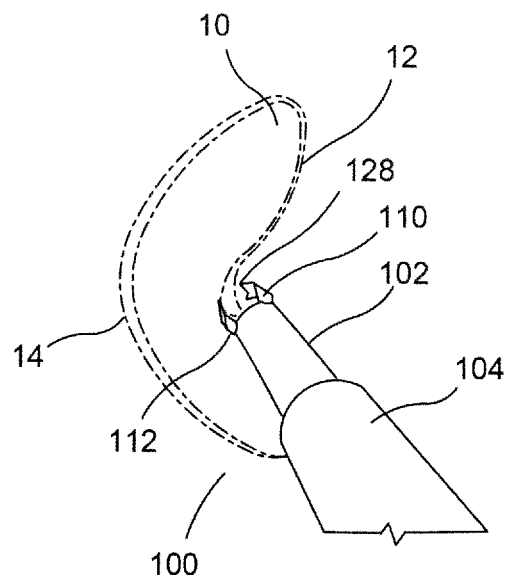
FIG. 13 shows a first step of a method of use of the clip system of FIG. 1.
Figure 14:
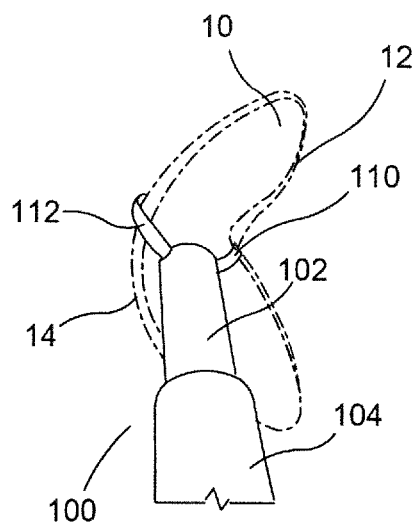
FIG. 14 shows a second step of the method of use of the clip system of FIG. 1.
Figure 15:
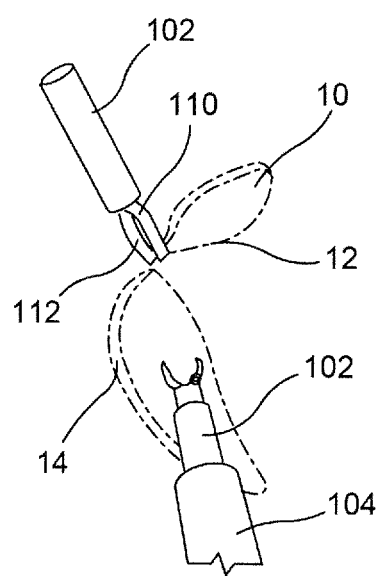
FIG. 15 shows a third step of the method of use of the clip system of FIG. 1.
Figure 16:
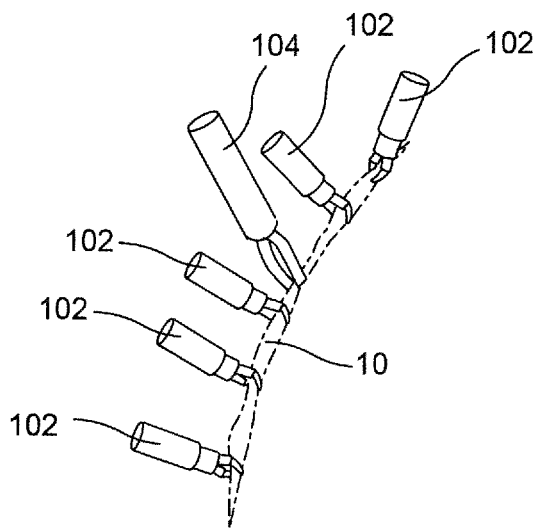
FIG. 16 shows a fourth step of the method of use of the clip system of FIG. 1.

In addition to spikes, hooks and barbs, other geometries can be used to improve attachment of clip arms to the target tissue defect. For example, in another exemplary embodiment, a clip assembly 402 of a clip system 400, shown in FIGS. 10-12, includes sharp teeth 440 at the distal tip 430 of at least one of first and second clip arms 410, 412. For example, as can be seen in FIGS. 11-12, the first clip arm 410 includes three teeth 440 positioned at an inner surface of the distal tip 430 of the first clip arm 410. It is noted that while this embodiment includes three teeth, any number of teeth may be used, as would be understood by those skilled in the art. The teeth 440 have sharpened tips to allow for tissue piercing and retention. Additionally, the distal tip 430 of the first clip arm 410 may be angled at approximately 90 degrees relative to the remainder of the clip arm 410 to allow for tissue retention when the clip arms 410, 412 are reopened.

A method of use of system 100 according to an exemplary embodiment is depicted in FIGS. 13-16. Initially, the clip assembly 102 is inserted through a working channel of an endoscope (or any other insertion device) and inserted into the body (e.g., through a natural body lumen) to a site adjacent to a target defect 10 of tissue to be clipped closed. The clip assembly 102 is inserted to the target tissue in the closed configuration to facilitate its passage through the working channel. Upon reaching the site of the target tissue defect, the clip assembly 102 is advanced out of the distal end of the working channel of the endoscope and the clip arms 110, 112 are extended out of the capsule 116 to move the clip arms 110, 112 to the open tissue receiving configuration. Once a first edge 12 of the tissue defect target tissue has been received between the clip arms 110, 112, the clip arms 110, 112 are moved toward the closed configuration so that the spikes 128 pierce the first edge 12 of the tissue defect so that the first edge 12 is gripped between distal ends of the clip arms 110, 112. The clip arms 110, 112 are moved toward the tissue gripping configuration by drawing the control member proximally with respect to the capsule 116. Once the clip assembly 102 is in the closed tissue gripping configuration, the first edge 12 is dragged towards the second edge 14 of the defect via the clip assembly 102, via the applicator 104. When the first and second edges 12, 14 of the tissue defect are adjacent to one another, the clip arms 110, 112 are gently reopened. As the clip arms 110, 112 are reopened, the first arm 110 releases the first edge 12 of the tissue defect but the two spikes 128 of the second clip arm 112 keep the first edge 12 attached to the second clip arm 112. The clip arms 110, 112 are subsequently re-closed over both edges 12, 14 of the tissue defect and the first clip assembly 102 is deployed from the applicator 104 via the actuator. Additional clip assemblies 102 may be placed along the tissue edges to close the defect.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

What is claimed is:

1. A system for treating tissue, comprising:
   a capsule extending longitudinally from a proximal end to a distal end and including a channel extending therethrough; and
   first and second clip arms each extending from a proximal end to a distal end, the proximal ends being received within the channel of the capsule to be moved between an open tissue receiving configuration, in which distal ends of the clip arms are separated from one another, and a closed tissue clipping configuration, in which distal ends of the clip arms are moved toward one another,
   wherein the first clip arm includes a first tissue retention feature at a distal portion thereof configured to pierce through a target tissue when in the tissue clipping configuration and subsequently release the target tissue when the clip arms are moved to an at least partially open configuration and the second clip arm includes a second tissue retention feature at a distal portion thereof configured to pierce and retain the target tissue thereon when in both the closed tissue clipping configuration and the open tissue receiving configuration.

2. The system of claim 1, wherein the first tissue retention feature includes at least one spike at a distal tip of the first arm and the second tissue retention feature includes two spikes at a distal tip of the second arm.

3. The system of claim 2, wherein the spikes extend from the distal tips of the first and second arms at a 90 degrees angle relative to the longitudinal axis of the clip arms.

4. The system of claim 1, wherein when the clip arms are in the closed configuration, spikes on opposing clip arms are configured to be staggered.

5. The system of claim 1, wherein the first tissue retention feature includes at least one spike at a distal tip of the first arm and the second retention feature includes at least one hook extending from the distal tip of the second arm.

6. The system of claim 1, wherein the second tissue retention feature includes a plurality of barbs extending from one of an interior surface and a side surface of the second clip arm.

7. The system of claim 6, wherein at least one of the barbs extends at a 90 degrees angle relative to a longitudinal axis of the second clip arm.

8. A reloadable clip device, comprising:
an applicator including a catheter and a control member extending therethrough, the control member extending from a proximal end to a distal end and being longitudinally movable relative to the applicator;
at least one clip assembly coupled to the applicator, each clip assembly comprising:
a capsule extending longitudinally from a proximal end to a distal end and including a channel extending therethrough; and
first and second clip arms each extending from a proximal end to a distal end, the proximal ends being received within the channel of the capsule to be moved between an open tissue receiving configuration, in which distal ends of the clip arms are separated from one another, and a closed tissue clipping configuration, in which distal ends of the clip arms are moved toward one another,
wherein the first clip arm includes a first tissue retention feature at a distal portion thereof configured to pierce through a target tissue when in the tissue clipping configuration and subsequently release the target tissue when the clip arms are moved to an at least partially open configuration and the second clip arm includes a second tissue retention feature at a distal portion thereof configured to pierce and retain the target tissue thereon when in both the closed tissue clipping configuration and the open tissue receiving configuration.

9. The system of claim 8, wherein the first tissue retention feature includes at least one spike at a distal tip of the first arm and the second tissue retention feature includes two spikes at a distal tip of the second arm.

10. The system of claim 9, wherein the spikes extend from the distal tips of the first and second arms at a 90 degrees angle relative to the longitudinal axis of the clip arms.

11. The system of claim 8, wherein when the clip arms are in the closed configuration, spikes on opposing clip arms are configured to be staggered.

12. The system of claim 8, wherein the first tissue retention feature includes at least one spike at a distal tip of the first arm and the second retention feature includes at least one hook extending from the distal tip of the second arm.

13. The system of claim 8, wherein the second tissue retention feature includes a plurality of barbs extending from one of an interior surface and a side surface of the second clip arm.

14. The system of claim 13, wherein at least one of the barbs extends at a 90 degrees angle relative to a longitudinal axis of the second clip arm.

15. The system of claim 13, wherein an interior surface of the first clip arm is flat.

16. A method of treating tissue, comprising:
inserting a first clip assembly to a target site within a living body via a working channel of an endoscope, the first clip assembly including a capsule and first and second clip arms slidably received within the capsule to be movable between an open configuration, in which distal ends of the clip arms are separated from one another, and a closed configuration, in which distal ends of the clip arms are drawn toward one another;
positioning the clip arms in contact with a first target tissue;
moving the first clip assembly from the open configuration to the closed configuration such that a first tissue retention feature on a distal portion of the first clip arm and a second tissue retention feature on a distal portion of the second clip arm pierces through the first target tissue;
moving the first clip assembly from the closed configuration to the open configuration, the first tissue retention feature releasing the first target tissue while the second tissue retention feature retains the first target tissue thereon;
positioning the clip arms in contact with a second target tissue; and
moving the first clip assembly from the open configuration to the closed configuration to clip the first and second target tissues between the first and second clip arms.

17. The method of claim 16, wherein the first tissue retention feature is a spike.

18. The method of claim 16, wherein the second tissue retention feature is one of a plurality of barbs, a plurality of spikes and a hook.

19. The method of claim 16, further comprising:
loading a first clip assembly on an applicator by coupling a control member of the applicator to the proximal ends of clip arms.

20. The method of claim 18, further comprising:
releasing the clip assembly from the applicator; and
loading a second clip assembly on an applicator by coupling a control member of the applicator to the proximal ends of clip arms.

* * * * *